(12) United States Patent
Yamada et al.

(10) Patent No.: US 11,846,620 B2
(45) Date of Patent: Dec. 19, 2023

(54) NOISE REMOVING APPARATUS, NOISE REMOVING METHOD, AND RECORDING MEDIUM

(71) Applicant: NEC Corporation, Tokyo (JP)

(72) Inventors: So Yamada, Tokyo (JP); Junko Watanabe, Tokyo (JP); Riki Eto, Tokyo (JP); Hiromi Shimizu, Tokyo (JP); Noriyuki Tonouchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/908,968

(22) PCT Filed: Mar. 17, 2020

(86) PCT No.: PCT/JP2020/011649
§ 371 (c)(1),
(2) Date: Sep. 2, 2022

(87) PCT Pub. No.: WO2021/186532
PCT Pub. Date: Sep. 23, 2021

(65) Prior Publication Data
US 2023/0110600 A1 Apr. 13, 2023

(51) Int. Cl.
*G01N 33/00* (2006.01)
*G01N 19/00* (2006.01)
*G01N 27/12* (2006.01)
*G01N 5/02* (2006.01)

(52) U.S. Cl.
CPC . *G01N 33/0062* (2013.01); *G01N 2033/0068* (2013.01)

(58) Field of Classification Search
CPC .............. G01N 33/0062; G01N 27/12; G01N 2033/0068; G01N 19/00; G01N 5/02; G01N 33/0031; G01N 33/0001; G01N 33/0027; G01N 1/22; G01N 1/38; G01N 1/405; G05B 15/02; G05B 19/042; A61L 2/26; G06N 20/00
USPC ... 73/1.06, 23.2, 23.34, 23.36, 31.01, 31.05; 422/83; 700/19, 28–31, 48, 90; 702/1, 702/19, 22–25, 27, 30–32, 104, 181, 183, 702/188–189; 703/11; 706/12–15, 45
See application file for complete search history.

(56) References Cited

U.S. PATENT DOCUMENTS

| 10,859,553 B2 * | 12/2020 | Yamasaki | G01N 33/03 |
| 2020/0003543 A1 * | 1/2020 | Trenholm | A61B 5/00 |
| 2021/0003543 A1 | 1/2021 | Hattori et al. | |

FOREIGN PATENT DOCUMENTS

| JP | H07-225184 A | 8/1995 | |
| JP | 2004-093241 A | 3/2004 | |
| JP | 3865409 B2 * | 1/2007 | ....... G01N 33/54373 |

(Continued)

OTHER PUBLICATIONS

International Search Report for PCT Application No. PCT/JP2020/011649, dated Jun. 23, 2020.

*Primary Examiner* — Jeffrey P Aiello (57) ABSTRACT

In a noise removing apparatus, a data acquisition unit acquires sets of odor data measured using a sensor with respect to a plurality of objects, each set of odor data representing features of an odor of an object by respective rates of a plurality of odor molecules. A noise component extraction unit extract a noise component using a set of odor data. A noise removing unit removes the noise component from each set of odor data to be processed.

10 Claims, 11 Drawing Sheets

(56) References Cited

FOREIGN PATENT DOCUMENTS

| JP | 2010-145258 A | 7/2010 |
|----|----|----|
| JP | 2017-156254 A | 9/2017 |
| WO | 2019/187671 A1 | 10/2019 |
| WO | 2020/026328 A1 | 2/2020 |
| WO | WO-2020026328 A1 * | 2/2020 |

* cited by examiner

TIME SERIES DATA AT TIME OF DETECTION: $Y=(y(t_1), y(t_2), ..., y(t_T))$

(REFERENCE DATE)                    (PROCESS TARGET DATE)

A

2019_6_12_110730_tea1.data          2019_6_13_190308_tea4.data

2019_6_12_111258_tea2.data          2019_6_13_190823_tea2.data
                              B
2019_6_12_111754_tea3.data          2019_6_13_191719_tea3.data 2019_6_12_112337_tea4.data          2019_6_13_192313_tea5.data

2019_6_12_112915_tea5.data          2019_6_13_193112_tea6.data

2019_6_12_113510.tea6.data          2019_6_13_1937424.tea1.data

2019_6_12_114146_tea7.data          2019_6_13_194454_tea7.data

2019_6_12_114631_tea8.data          2019_6_13_195226_tea8.data

\* NOISE COMPONENT (N)
  = FIRST DATA (A) OF PROCESS TARGET DATE
  − DATA (B) OF REFERENCE DATE FOR SAME LABEL

(AVERAGE CALCULATION DATE)

(2019_6_10)
2019_6_10_110730_tea1.data
2019_6_10_111258_tea2.data
2019_6_10_111754_tea3.data
2019_6_10_112337_tea4.data
2019_6_10_112915_tea5.data
2019_6_10_113510_tea6.data
2019_6_10_114146_tea7.data
2019_6_10_114631_tea8.data (2019_6_11)
2019_6_11_172621_tea1.data
2019_6_11_173212_tea2.data
2019_6_11_174056_tea3.data
2019_6_11_174629_tea4.data
2019_6_11_175234_tea5.data
2019_6_11_180626.tea6.data
2019_6_11_18155_tea7.data
2019_6_11_181709_tea8.data

(2019_6_12)
2019_6_12_190308_tea1.data
2019_6_12_190823_tea2.data
2019_6_12_191719_tea3.data
2019_6_12_192313_tea4.data
2019_6_12_193112_tea5.data
2019_6_12_193742.tea6.data
2019_6_12_193454.tea7.data
2019_6_12_195226_tea8.data

⇒ CALCULATE AVERAGE DATA M (PROCESS TARGET DATE)
2019_6_13_190308_tea4.data  ← A
2019_6_13_190823_tea2.data
2019_6_13_191719_tea3.data
2019_6_13_192313_tea5.data
2019_6_13_193112_tea6.data
2019_6_13_1937424.tea1.data
2019_6_13_194454_tea7.data
2019_6_13_195226_tea8.data

* NOISE COMPONENT (N)
= FIRST DATA (A) OF PROCESS TARGET DATE
− AVERAGE DATA (M) FOR SAME LABEL

(PROCESS TARGET DATE)

2019_6_12_110730_tea1.data
2019_6_12_111258_tea2.data
2019_6_12_111754_tea3.data
2019_6_12_112337_tea4.data
2019_6_12_112915_tea5.data
2019_6_12_113510.tea6.data
2019_6_12_114146_tea7.data  D
2019_6_12_114631_tea8.data DETERMINE LABEL D
TO BE SUBTRACTED
EXAMPLE: tea8

SUBTRACT DATA OF
LABEL D FROM EACH OF
OTHER LABELS

FIG. 12

<THIRD EXAMPLE OF FIRST EXAMPLE EMBODIMENT>

FIG. 13

NOISE REMOVING APPARATUS, NOISE REMOVING METHOD, AND RECORDING MEDIUM

This application is a National Stage Entry of PCT/JP2020/011649 filed on Mar. 17, 2020, the contents of all of which are incorporated herein by reference, in their entirety.

TECHNICAL FIELD

The present disclosure relates to a technique for removing noises from odor data measured using a sensor.

BACKGROUND ART

A technique for detecting odor using a sensor is known. As an odor sensor, for example, a semiconductor type sensor, a crystal oscillation type sensor, a membrane type surface stress sensor and the like are known. Patent Document 1 describes a technique for measuring a sample gas using a nanomechanical sensor provided with a receptor layer, and discriminating a type of the sample gas.

PRECEDING TECHNICAL REFERENCES

Patent Document

Patent Document 1: Japanese Laid-open Patent Publication No. 2017-156254

SUMMARY

Problem to be Solved by the Invention

An odor measurement technique using a membrane type surface stress sensor detects deflection of a detection film when odor molecules attach to the detection film such as silicon, and outputs a voltage change depending on the deflection. However, an ease of adhesion and desorption of odor molecules with respect to the detection membrane, a rate thereof, and the like are affected by environmental conditions such as temperature and humidity. Also, in a case of successively performing measurements, although a process of exhausting a gas from a space such as a container, in which the sensor is disposed, is usually performed, it is difficult to completely remove such a residual gas by this process.

It is one object of the present disclosure to remove, from the odor data measured by the odor sensor, noise components caused by changes of environmental conditions and the residual gas.

Means for Solving the Problem

According to an example aspect of the present disclosure, there is provided a noise removing apparatus including:
  a data acquisition unit configured to acquire sets of odor data measured using a sensor with respect to a plurality of objects, each set of odor data representing features of an odor of an object by respective rates of a plurality of odor molecules;
  a noise component extraction unit configured to extract a noise component using a set of odor data; and
  a noise removing unit configured to remove the noise component from each set of odor data to be processed.

According to another example aspect of the present disclosure, there is provided a noise removing method, including:
  acquiring sets of odor data measured using a sensor with respect to a plurality of objects, each set of odor data representing features of an odor of an object by respective rates of a plurality of odor molecules;
  extracting a noise component using a set of odor data; and
  removing the noise component from each set of odor data to be processed.

According to still another example aspect of the present disclosure, there is provided a recording medium storing a program, the program causing a computer to perform a process including:
  acquiring sets of odor data measured using a sensor with respect to a plurality of objects, each set of odor data representing features of an odor of an object by respective rates of a plurality of odor molecules;
  extracting a noise component using a set of odor data; and
  removing the noise component from each set of odor data to be processed.

Effect of the Invention

According to the present disclosure, it becomes possible to remove, from odor data measured by an odor sensor, noise components caused by changes of environmental conditions and a residual gas.

EXAMPLE EMBODIMENTS

In the following, example embodiments will be described with reference to the accompanying drawings.

First Example Embodiment

[Overall Configuration]

Figure 1:
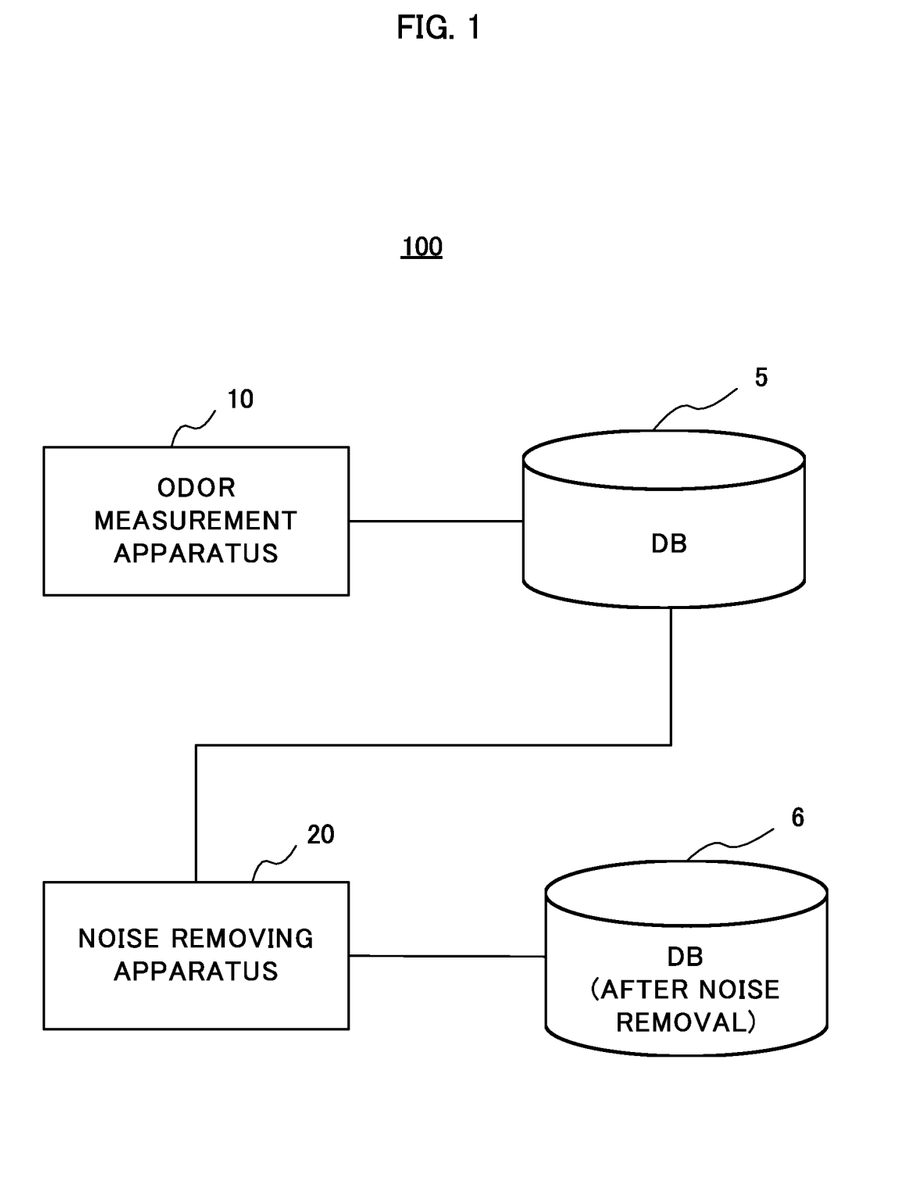
FIG. 1 illustrates a configuration of an odor measurement system according to a first example embodiment of the present disclosure.

FIG. 1 illustrates a configuration of an odor measurement system according to a first example embodiment of the present disclosure. An odor measurement system 100 includes an odor measurement apparatus 10, a database (hereinafter, also referred to as a "DB") 5, a noise removing apparatus 20, and a DB 6. The odor measurement apparatus 10 measures an odor of an object, and outputs odor data. The odor data are temporarily stored in the DB 5. The noise removing apparatus 20 performs a noise removal of the odor data stored in the DB 5, and stores the odor data after the noise removal in the DB 6. The odor data stored in the DB 6 are subjected to a subsequent process, for instance, for analyzing an odor component.

[Odor Measurement Apparatus]

Figure 2A:
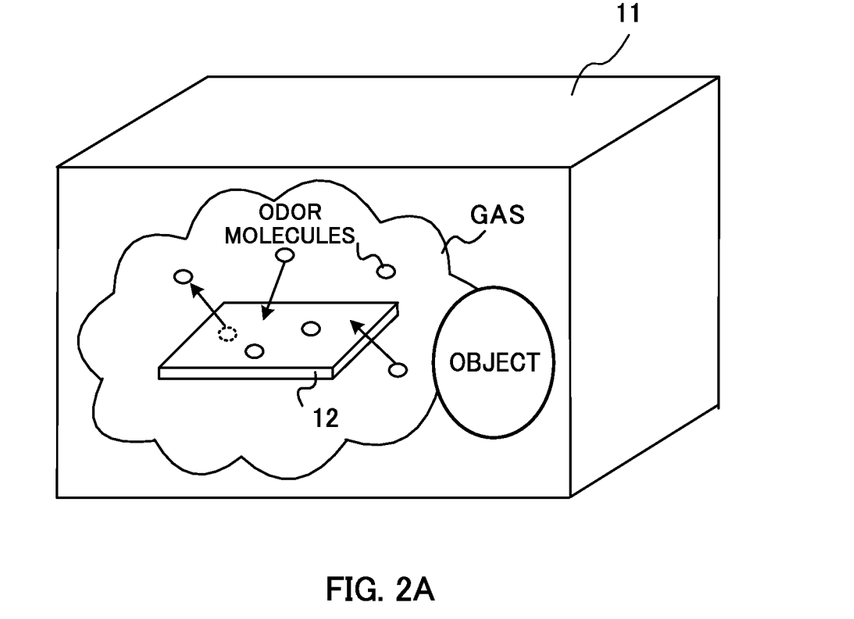
FIG. 2 schematically illustrates a principle of an odor measurement apparatus.
Figure 2B:
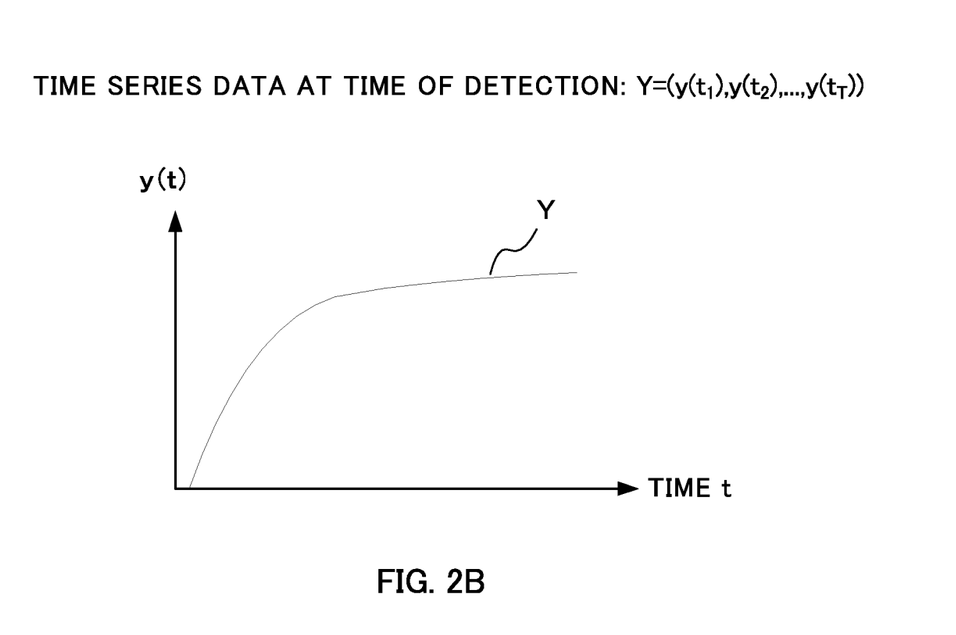

The odor measurement apparatus 10 measures an odor of an object using a sensor, and outputs odor data. FIG. 2A schematically illustrates a principle of the odor measurement apparatus 10. The odor measurement apparatus 10 includes a housing 11 and a sensor 12 disposed in the housing 11. The sensor 12 has receptors to which odor molecules attach, and a detected value changes in response to attachments and detachments of the molecules at those receptors. The object to be a subject for an odor measurement is disposed in the housing 11. The odor molecules contained in a gas present in the housing 11 adhere to the sensor 12. Hereinafter, the gas being sensed by the sensor 12 is referred to as a "target gas". Furthermore, time series data of the detected value, which is output from the sensor 12, are represented by "time series data Y". When the detected value of a time t of the time series data Y is denoted as y(t), as illustrated in FIG. 2B, the time series data Y are a vector formed by the detected value y(t) at each time.

The sensor 12 is a membrane-type surface stress (MSS: Membrane-type Surface Stress) sensor. The MSS sensor has, as the receptors, a functional film to which molecules adhere, and a stress generated in a support member of the functional film changes due to the attachments and the detachments of the odor molecules to the functional film. The MSS sensor outputs a detected value based on this change in this stress. The sensor 12 is not limited to the MSS sensor, and may be any one that outputs a detected value based on a variation in a physical quantity related to a viscoelasticity or a dynamic property (a mass, a moment of inertia, or the like) of a member of the sensor 12 that occurs in response to the attachments and the detachments of the molecules with respect to the receptors. For instance, one of various types of sensors may be employed, such as a cantilever type, a membrane type, an optical type, a piezo, a vibration response, and the like.

For the sake of explanation, sensing by the sensor 12 is modeled as follows.

(1) The sensor 12 is exposed to a target gas containing k types of molecules.

(2) A concentration for each of the k types of molecules in the target gas is a constant $\rho_k$.

(3) A total of n molecules can be adhered to the sensor 12.

(4) The number of the molecules k attached to the sensor 12 at a time t is denoted by $n_k(t)$.

In this case, a change in the number $n_k(t)$ of the molecules k attached to the sensor 12 over time can be formulated as follows.

[Math 1]

$$\frac{dn_k(t)}{dt} = \alpha_k \rho_k - \beta_k n_k(t) \tag{1}$$

Each of a first term and a second term on a right side of the above formula (1) represents an increase amount of the molecules k per unit time (a number of the molecules k newly attaching to the sensor 12) and a decrease amount of the molecules k per unit time (a number of the molecules k detaching from the sensor 12). Moreover, $\alpha_k$ denotes a rate constant representing a velocity at which the molecules k attach to the sensor 12, and $\beta_k$ denotes a rate constant representing a velocity at which the molecules k detach from the sensor 12.

Here, since the concentration $\rho_k$ is constant, the number $n_k(t)$ of the molecules k at the time t from the above formula (1) can be formulated as follows.

[Math 2]

$$n_k(t) = n_k^* + (n_k(t_0) - n_k^*)e^{\beta_k t} \tag{2}$$

however, $$n_k^* = \frac{\beta_k \rho_k}{\alpha_k}$$

Furthermore, assuming that no molecule is attached to the sensor 12 at a time $t_0$ (an initial state), $n_k(t)$ is expressed as follows.

[Math 3]

$$n_k(t) = n_k^* (1 - e^{-\beta_k t}) \tag{3}$$

The detected value of the sensor 12 is determined by a stress exerted on the sensor 12 by the molecules contained in the target gas. Accordingly, it is considered that the stress exerted on the sensor 12 by a plurality of molecules can be represented by a linear sum of stresses generated by individual molecules. However, it is considered that a stress generated by each molecule varies depending on a type of the molecule. That is, a contribution of the molecule with respect to the detected value of the sensor 12 differs depending on the type of the molecule.

Therefore, the detected value y(t) of the sensor 12 can be formulated as follows.

[Math 4]

$$y(t) = \sum_{k=1}^{K} \gamma_k n_k(t) \tag{4}$$

$$= \begin{cases} \xi_0 - \sum_{k=1}^{K} \xi_k e^{-\beta_k t} & \text{(rising case)} \\ \sum_{k=1}^{K} \xi_k e^{-\beta_k t} & \text{(falling case)} \end{cases}$$

however,

-continued $$\xi_k = \frac{\gamma_k \alpha_k \rho_k}{\beta_k} (k = 1, \ldots, K), \xi_0 = \sum_{k=1}^{K} \xi_k$$

Here, both $\gamma_k$ and $\xi_k$ represent contributions of a molecule k with respect to the detected value of the sensor 12. Note that the "rising case" refers to a case of exposing the sensor 12 to the target gas, and the "falling case" refers to a case of removing the target gas from the sensor 12. Note that an operation of removing the target gas from the sensor is performed, for instance, by exposing the sensor to a gas called purge gas.

Here, in a case where the time series data Y obtained by the sensor 12 in which the target gas is sensed can be decomposed as in the above formula (4), it is possible to comprehend the types of the molecules contained in the target gas and a rate of each of the types of the molecules contained in the target gas. That is, by the decomposition represented by the formula (4), data representing features of the target gas, that is, a feature amount of the target gas can be obtained.

Therefore, the odor measurement apparatus 10 acquires the time series data Y output by the sensor 12, and decomposes as expressed in the following formula (5).

[Math 5]

$$y(t) = \sum_{i=1}^{m} \xi_i f(\theta_i) \quad (5)$$

Here, $\theta_i$ denotes a time constant or a rate constant with respect to a magnitude of a change in an amount of the molecules adhering to the sensor 12 over time. $\xi_i$ denotes a contribution value representing a contribution of the feature constant $\theta_i$ to the detected value of the sensor 12.

As a feature constant $\theta$, it is possible to adopt the aforementioned rate constant $\beta$ or a time constant $\tau$ which is an inverse of the rate constant. For each case where $\beta$ or $\tau$ is used as the feature constant $\theta$, the formula (5) can be expressed as follows.

[Math 6]

$$y(t) = \sum_{i=1}^{m} \xi_i e^{-\beta_i t} \quad (6)$$

$$y(t) = \sum_{i=1}^{m} \xi_i e^{-t/\tau_i} \quad (7)$$

Figure 3:
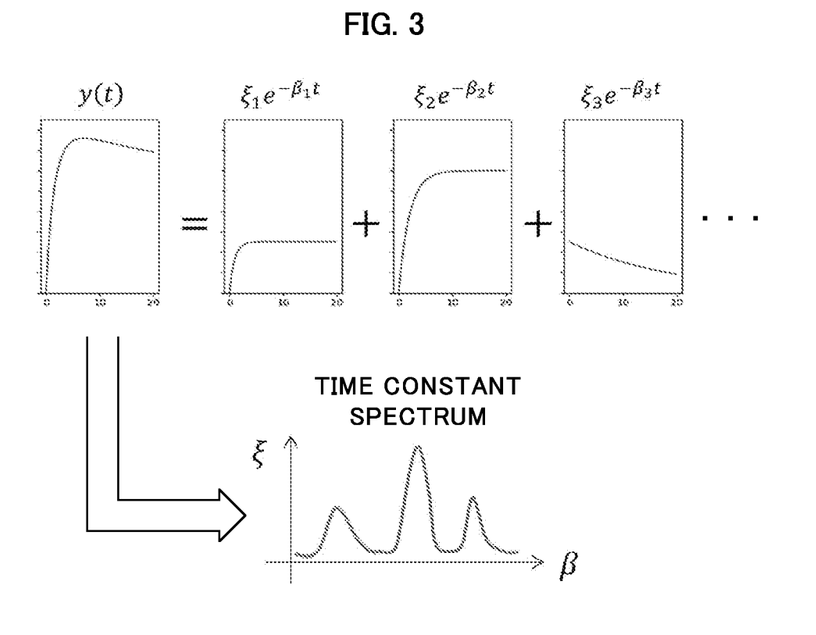
FIG. 3 is a diagram for explaining a time series spectrum.

Hereinafter, for convenience of explanation, it is assumed that the time series data Y are represented by the formula (6). As illustrated in FIG. 3, the time series data Y(t) can be expressed as a linear sum of components of each molecule. Therefore, the target gas, that is, an odor of an object can be represented by a graph (hereinafter, referred to as a "time constant spectrum") taking each of molecules on a horizontal axis and taking a contribution value $\xi$ of each of molecules on a vertical axis as illustrated in FIG. 3. In the time constant spectrum, the horizontal axis indicates the odor molecules contained in the target gas, and the vertical axis indicates a rate of the odor molecules for each type contained in the target gas, that is, the rate of the odor molecules for each of types forming an odor of the target gas. Accordingly, by analyzing the time constant spectrum, it is possible to investigate what kinds of components the odor of the object is composed of. The odor measurement apparatus 10 outputs the time constant spectrum as odor data for each object. Although an example of removing noises from data of the time constant spectrum will be described in the following, the odor data to be the target of a noise removal is not limited to the time constant spectrum, and raw waveform data before the time constant spectrum is generated may be used.

[Noise Removing Apparatus]

(Hardware Configuration)

Figure 4:
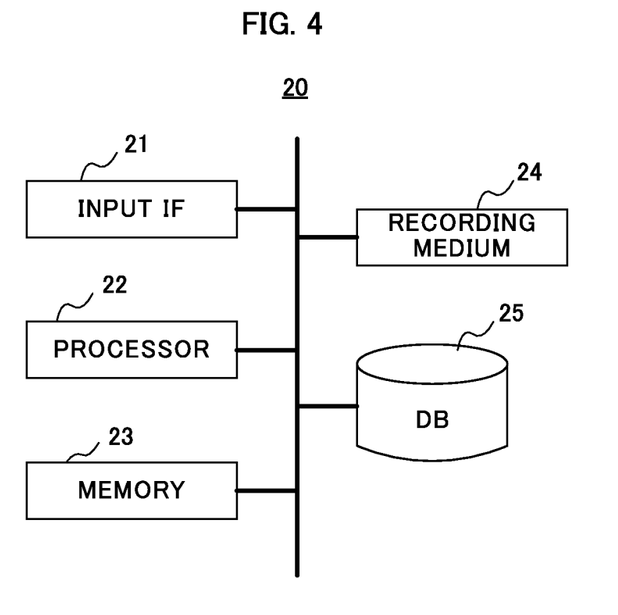
FIG. 4 illustrates a hardware configuration of a noise removing apparatus.

FIG. 4 is a block diagram illustrating a hardware configuration of a noise removing apparatus. As illustrated, the noise removing apparatus 20 includes an input IF (Interface) 21, a processor 22, a memory 23, a recording medium 24, and a database (DB) 25.

The input IF 21 inputs and outputs odor data. Specifically, the input IF 21 is used to acquire odor data from the DB 5 and to store the odor data after noises are removed in DB 6. The processor 22 is a computer such as a CPU (Central Processing Unit), and controls the entire noise removing apparatus 20 by executing programs prepared in advance. Specifically, the processor 22 executes a noise removal process which will be described later.

The memory 23 is formed by a ROM (Read Only Memory), a RAM (Random Access Memory), or the like. The memory 23 stores various programs to be executed by the processor 22. The memory 23 is also used as a working memory during the executions of various processes by the processor 22.

The recording medium 24 is a non-volatile and non-transitory recording medium such as a disk-shaped recording medium, a semiconductor memory, and is formed to be detachable from the noise removing apparatus 20. The recording medium 24 records various programs executed by the processor 22. When the noise removing apparatus 20 executes various processes, programs recorded in the recording medium 24 are loaded into the memory 23 and executed by the processor 22.

The DB 25 stores data input from an external apparatus including an input IF 21. Specifically, the DB 25 temporarily stores the odor data acquired from the DB 5.

(Functional Configuration)

Figure 5:
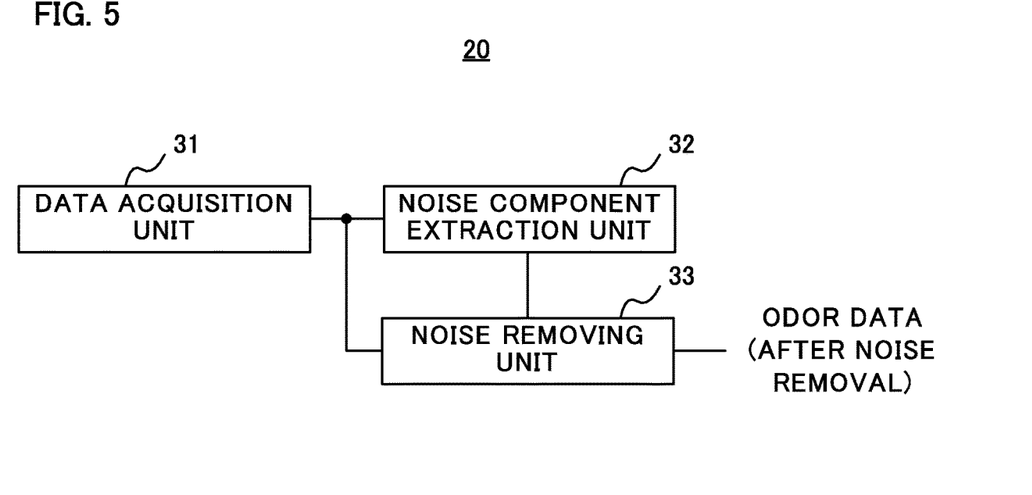
FIG. 5 illustrates a functional configuration of the noise removing apparatus.

FIG. 5 is a block diagram illustrating a functional configuration of the noise removing apparatus. The noise removing apparatus 20 functionally includes a data acquisition unit 31, a noise component extraction unit 32, and a noise removing unit 33. The data acquisition unit 31 acquires odor data prior to a noise removal from DB 5 and supplies the odor data to the noise component extraction unit 32 and the noise removing unit 33.

The noise component extraction unit 32 extracts a noise component based on the odor data. The noise component extraction unit 32 supplies the extracted noise component to the noise removing unit 33. The noise removing unit 33 removes the noise component from the odor data to be processed acquired from the data acquisition unit 31, and outputs the odor data after the noise removal. The odor data after the noise removal are stored in the DB 6.

Figure 6:
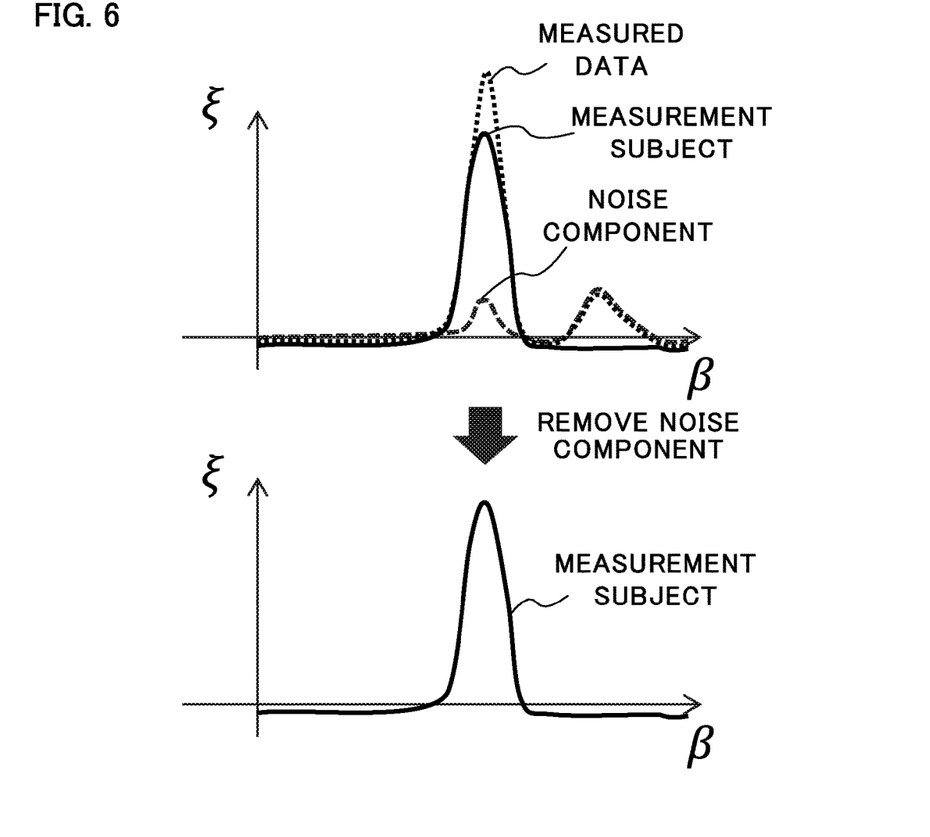
FIG. 6 is a diagram for explaining a noise component.

Here, the "noise component" is a concept including a variation of the odor data due to an environmental condition influencing on the odor measurement such as temperature or humidity, and a variation of the odor data due to a residual gas in the odor measurement apparatus 10. FIG. 6 is a diagram illustrating the noise component. The odor data output from the odor measurement apparatus 10 are regarded as data of the time constant spectrum as described above, and the noise component as described above is added in the data in addition to the components of the measurement target. Therefore, the noise component extraction unit 32 extracts the noise component mixed in the odor data, the noise removing unit 33 removes the noise component from the odor data of the process target, and outputs the odor data as a subject to be measured.

In the following, examples of the noise removing apparatus according to the first example embodiment.

First Example

Figure 7:
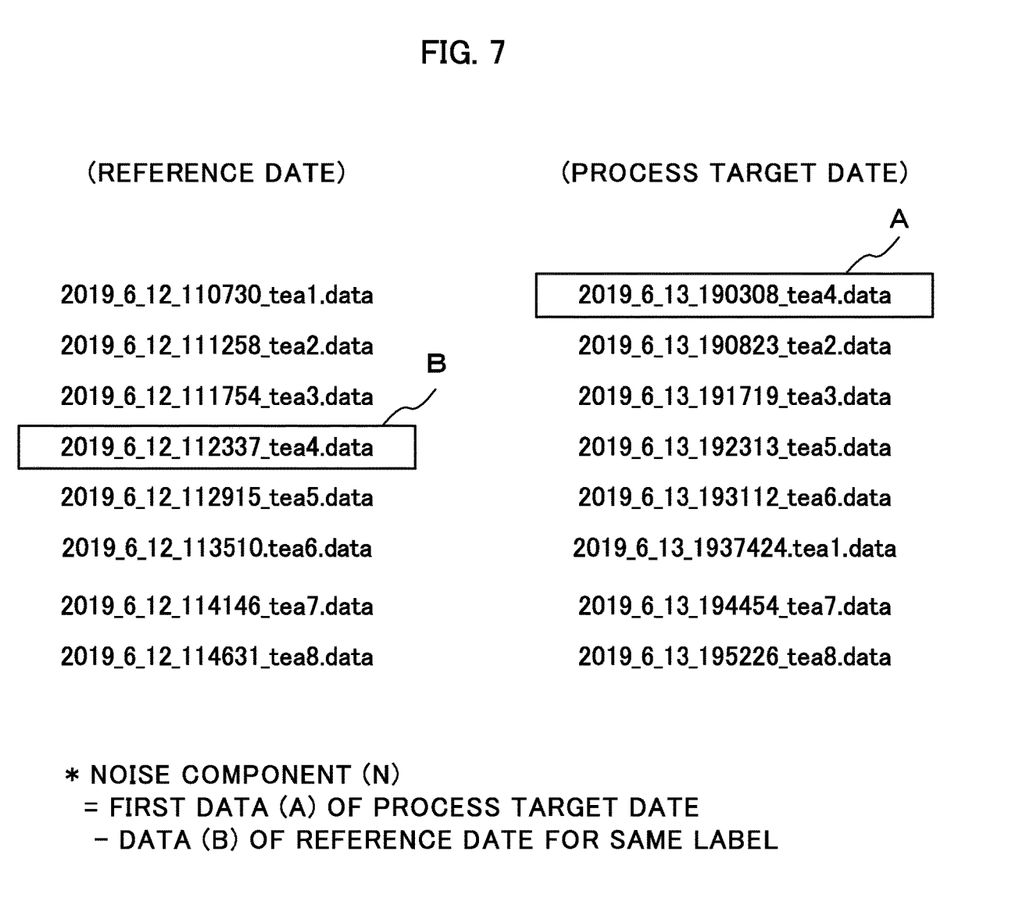
FIG. 7 is a diagram for explaining a noise removing method according to a first example of the first example embodiment.

FIG. 7 is a diagram illustrating a noise removing method according to a first example of the first example embodiment. Now, it is assumed that sets of odor data corresponding to eight types of teas are obtained by the odor measurement apparatus 10 as illustrated in the FIG. 7. The eight types of teas are identified by labels "tea1" through "tea8". In the first example embodiment, the noise component on a date (hereinafter referred to as a process target date.) for performing the noise removal process is extracted based on data of a reference date. Here, the "reference date" is a predetermined date, and it is preferable to select a date considered to be a condition of relatively low noise based on the environmental condition such as temperature or humidity. Since the environmental condition such as temperature or humidity that causes noises is considered not to vary so much on the same date, the noise component at the same date is regarded as constant. In the first example, a component, which is obtained by subtracting data at the reference date from first data at a process target date, is regarded as a noise component N at the process target date. In an example in FIG. 7, the noise component extraction unit 32 determines, as the noise component, a component in which data B of the reference date for the same label (that is, tea4) are subtracted from first data A of the process target date. That is, the noise component N is calculated by the following equation.

Noise component ($N$)=the first data at the process target date ($A$)–data ($B$) at the reference date of the same label (1)

Since the noise component N of the process target date is considered to be similarly included in data of each label of the process target date, the noise removing unit 33 subtracts the noise component N at the process target date from each data at the process target date, and thus generates odor data after the noise removal. Accordingly, for each of the eight types of teas, odor data after the noise removal is obtained.

Figure 8:
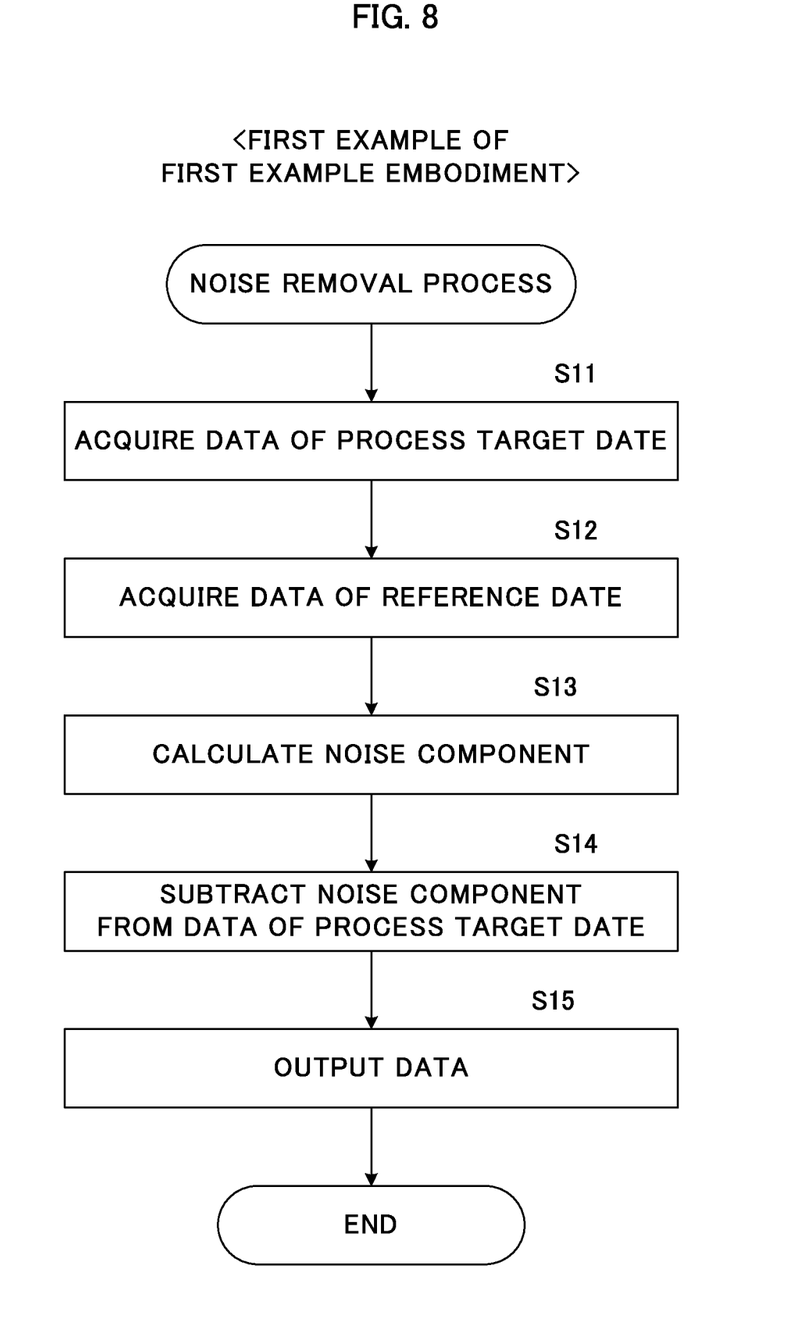
FIG. 8 is a flowchart of a noise removing process according to the first example of the first example embodiment.

FIG. 8 is a flowchart of the noise removal process according to the first example of the first example embodiment. This process is implemented by the processor 22 illustrated in FIG. 4, which executes a program prepared in advance. First, the data acquisition unit 31 acquires data of the process target date (step S11), and further acquires data of the reference date (step S12). An order of steps S11 and S12 may be reversed.

Next, the noise component extraction unit 32 uses the data of the process target date and the data of the reference date so as to calculates the noise component by the above equation (1) (step S13), and supplies the calculated noise component the noise removing unit 33. The noise removing unit 33 subtracts the noise component from the data of each label of the process target date (step S14), and outputs the odor data after the noise removal (step S15). After that, the noise removal process is terminated.

Second Example

Figure 9:
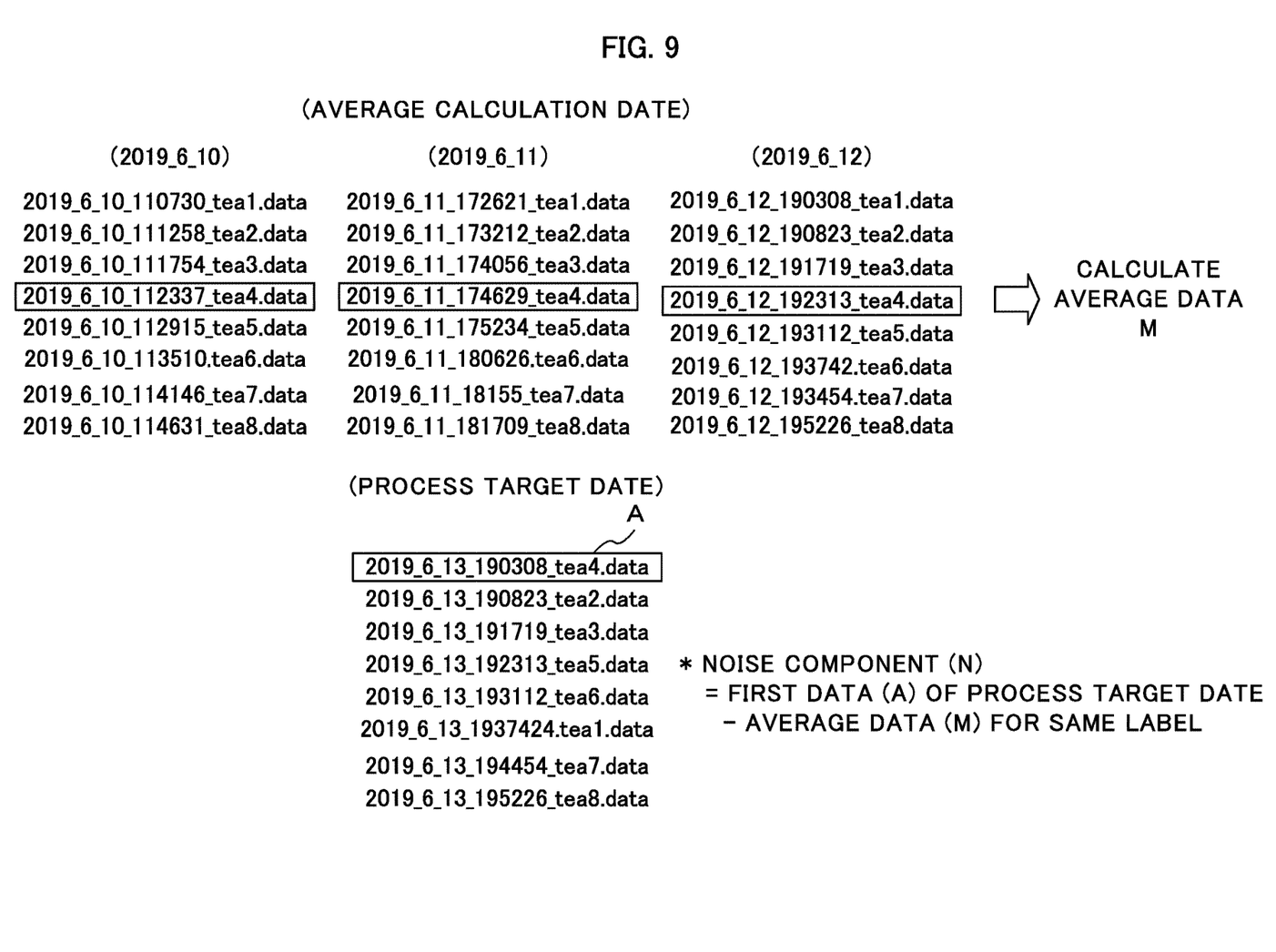
FIG. 9 is a diagram for explaining a noise removing method according to a second example of the first example embodiment.

FIG. 9 is a diagram illustrating a noise removal method according to a second example of the first example embodiment. In the second example, the noise component extraction unit 32 calculates the noise component using average data of a plurality of dates, instead of the data of the reference date. Specifically, first, the plurality of dates (hereinafter, referred to as "average calculation dates.") to calculate the average data are determined. For instance, the average calculation dates may be two dates, three dates, or the like before the process target date. The number of the average calculation dates may be changed according to a use of the odor data after the noise removal. For instance, in a case where the odor data after the noise removal are used as training data such as a model for predicting contained substances from the odor data, the average calculation dates are set to 2 dates, and in a case of using as test data of the model, the average calculation dates may be set to 3 dates. Note that in an example in FIG. 9, the average calculation dates are set to 3 dates.

The noise component extraction unit 32 specifies a label of the first data at the process target date, and calculates average data M for the same label. In the example in FIG. 9, since the label is "tea4" for the first data of the process target date, the noise component extraction unit 32 calculates the average data M of three sets of data for the same label "tea4" during the average calculation dates. The noise component extraction unit 32 extracts the noise component by subtracting the average data M for the same label from the first data A of the process target date. That is, the noise component N is calculated by the following equation.

Noise component ($N$)=the first data of the process target date ($A$)–average data ($M$) for the same label (2)

After that, similarly to the first example, the noise removing unit 33 subtracts the noise component N of the process target date from each set of data of the process target date, and generates odor data after the noise removal. By the above processes, for each of the eight types of teas, the odor data after the noise removal are obtained.

Figure 10:
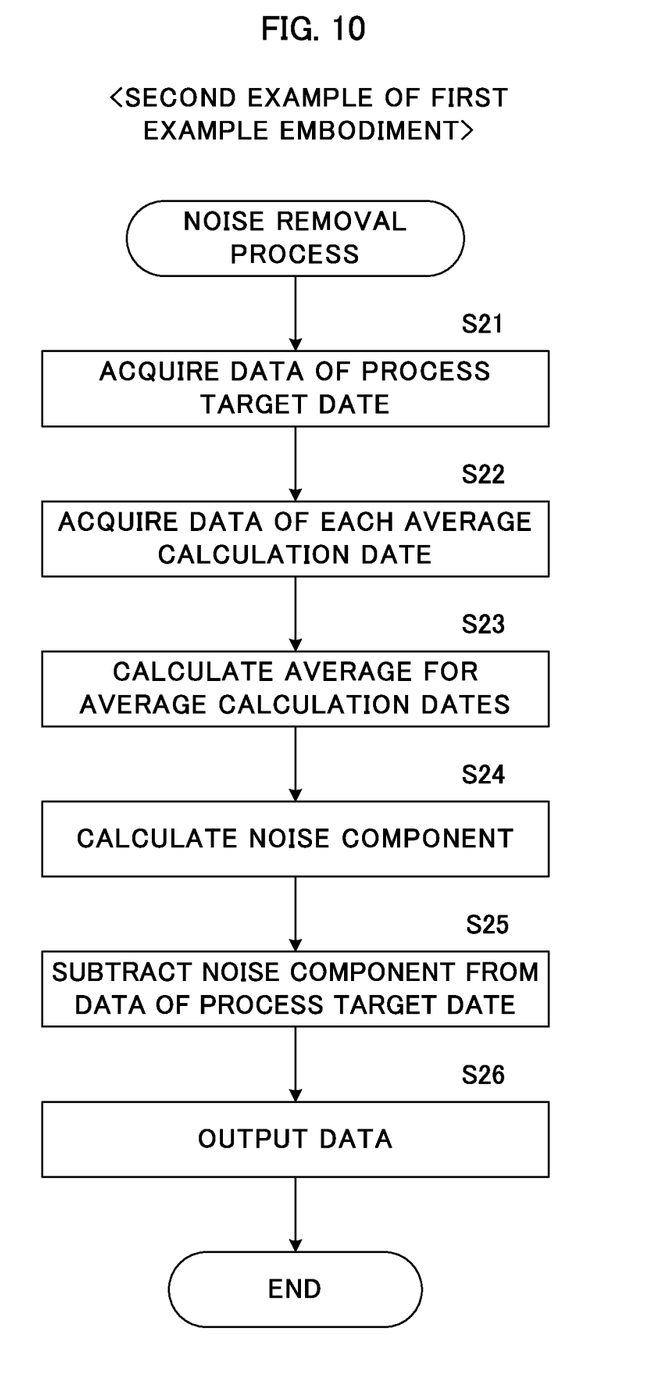
FIG. 10 is a flowchart of a noise removing process according to the second example of the first example embodiment.

FIG. 10 is a flowchart of the noise removal process according to the second example of the first example embodiment. This process is implemented by the processor 22 illustrated in FIG. 4, which executes a program prepared in advance. First, the data acquisition unit 31 acquires data of a process target date (step S21), and further obtains data of the average calculation date (step S22). An order of steps S21 and S22 may be reversed.

Next, the noise component extraction unit 32 calculates the average data M using sets of data during the average calculation dates for the same label as the first data of the process target date (step S23). Subsequently, the noise component extraction unit 32 calculates the noise component by subtracting the average data M from the first data of the process target date in accordance with the above equation (2) (step S24), and supplies the calculated noise component to the noise removing unit 33. The noise removing unit 33 subtracts the noise component from data of each label of the process target date (step S25), and outputs odor data after the noise removal (step S26). After that, the noise removal process is terminated.

In the above example, the noise component N is calculated by using the average data M during the average calculation dates; alternatively, another statistical value other than the average, for instance, data of a median value of the same label during the average calculation dates may be used.

Third Example

Figure 11:
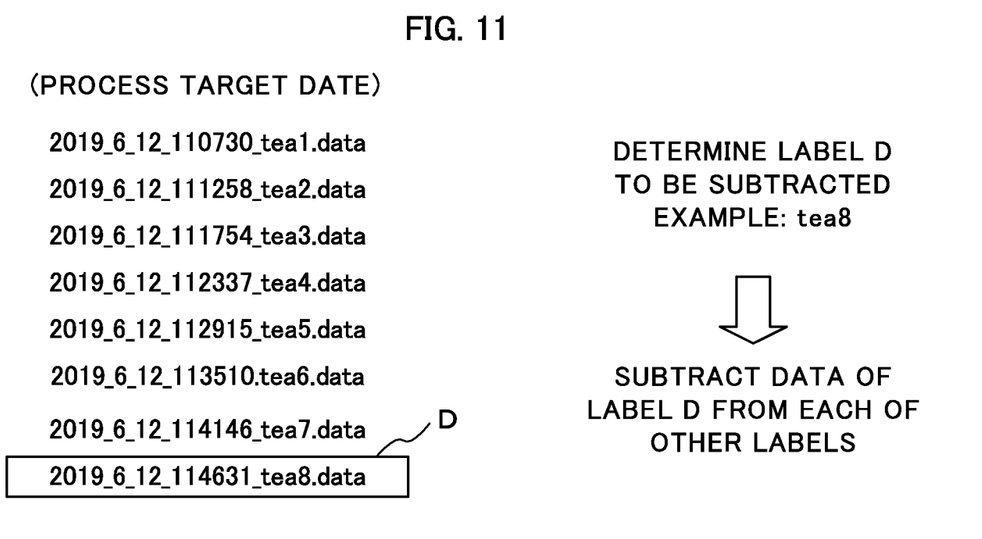
FIG. 11 is a diagram for explaining a noise removing method according to a third example of the first example embodiment.

FIG. 11 is a diagram illustrating a noise removal method according to a third example of the first example embodiment. In the third example embodiment, only the data of the process target date are used, one set of data among sets of data of a plurality of labels are included in a noise component, and the one set of data are subtracted from respective sets of data of other labels. As mentioned above, since respective noise components at the same date are basically considered to be the same, it can be considered that sets of data for eight types of labels of the process target date also contain the noise component of that date. Accordingly, the noise component is subtracted from data of each label by subtracting the data of one label containing the noise component of that date from each set of data of the other labels.

In an example in FIG. 11, the label "tea8" is subtracted with noise. In this case, data of the label "tea8" include not only the odor component contained in that tea but also the noise component of that date. Therefore, the data of the label "tea8" are subtracted from respective sets of data of other seven types of the labels "tea1" through "tea7". In this manner, from each set of data, the noise component of that date is subtracted along with the odor component of the tea of the label "tea8". By this subtraction, the noise component of the date can be removed from each data. Note that in this method, the odor component of the tea of "tea8" is also subtracted from each set of data for the seven types of labels "tea1" through "tea7"; however, since the odor component is similarly subtracted from each set of data for the labels "tea1" through "tea7", it is considered that there is no particular effect for a case of discriminating seven types of labels in a subsequent process. However, since the component of one label is subtracted from sets of data of other labels along with a noise component, it is possible to perform an odor classification of the seven types of odors based on the eight types of labels.

Figure 12:
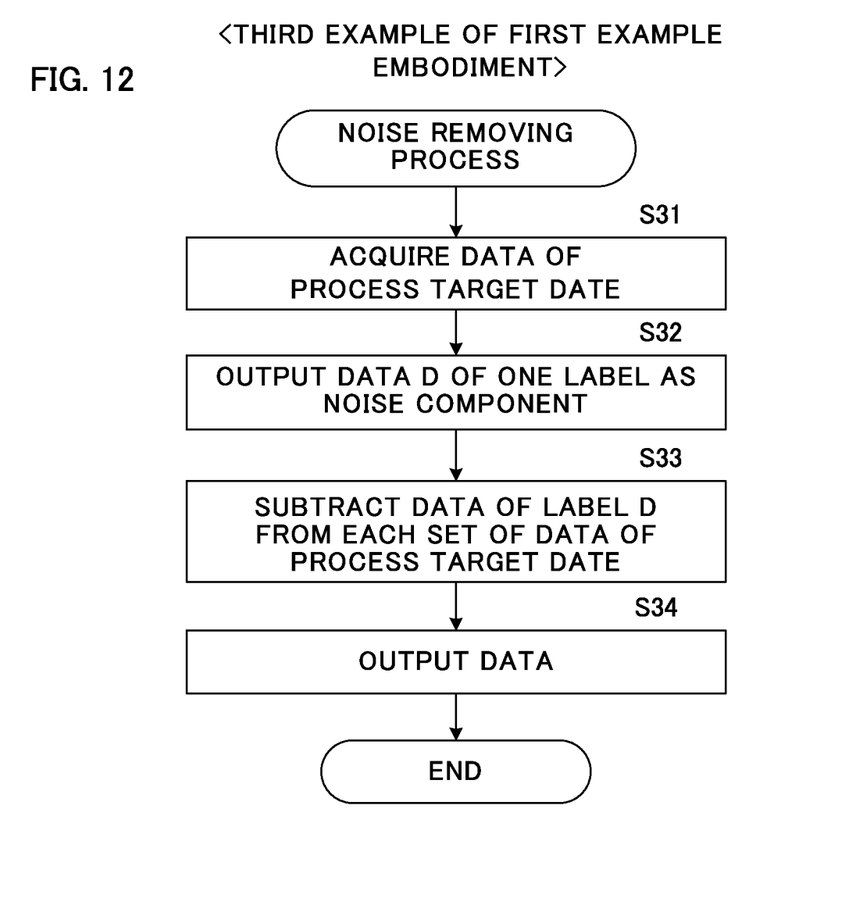
FIG. 12 is a flowchart of a noise removing process according to the third example of the first example embodiment.

FIG. 12 is a flowchart of a noise removal process according to a third example of the first example embodiment. This process is implemented by the processor 22 illustrated in FIG. 4, which executes a program prepared in advance. First, the data acquisition unit 31 acquires data of the process target date (step S31). Next, the noise component extraction unit 32 outputs data of one label D determined in advance as a noise component to the noise removing unit 33 (step S32). The noise removing unit 33 subtracts the data of the label D from respective sets of data of other labels (step S33), and outputs data after the noise removal as odor data (step S34). After that, the noise removal process is terminated.

As described above, in the technique of the third example embodiment, the component of one label is subtracted with the noise from the sets of data of the other labels, so that the number of labels to be subjected to a subsequent determination process is reduced by one. Therefore, a label for a purpose of subtracting with noise may be prepared separately. For instance, a label "water" is prepared to be subtracted along with noise, and odor data concerning water are also measured on the process target date. The measured water data include an odor component of the water and a noise component of the process target date. Therefore, by subtracting the data of the label "water" from each set of data of the eight labels illustrated in FIG. 11, it is possible to obtain the data after the noise removal concerning the eight labels.

Second Example Embodiment

Next, a second example embodiment of the present disclosure will be described. In the second example embodiment, in a case where the odor measurement apparatus 10 measures odors of different objects in order, components such as a residual gas and the like are removed as noise components. Note that, a configuration of an odor measurement system according to the second example embodiment is the same as that in the first example embodiment.

Figure 13:
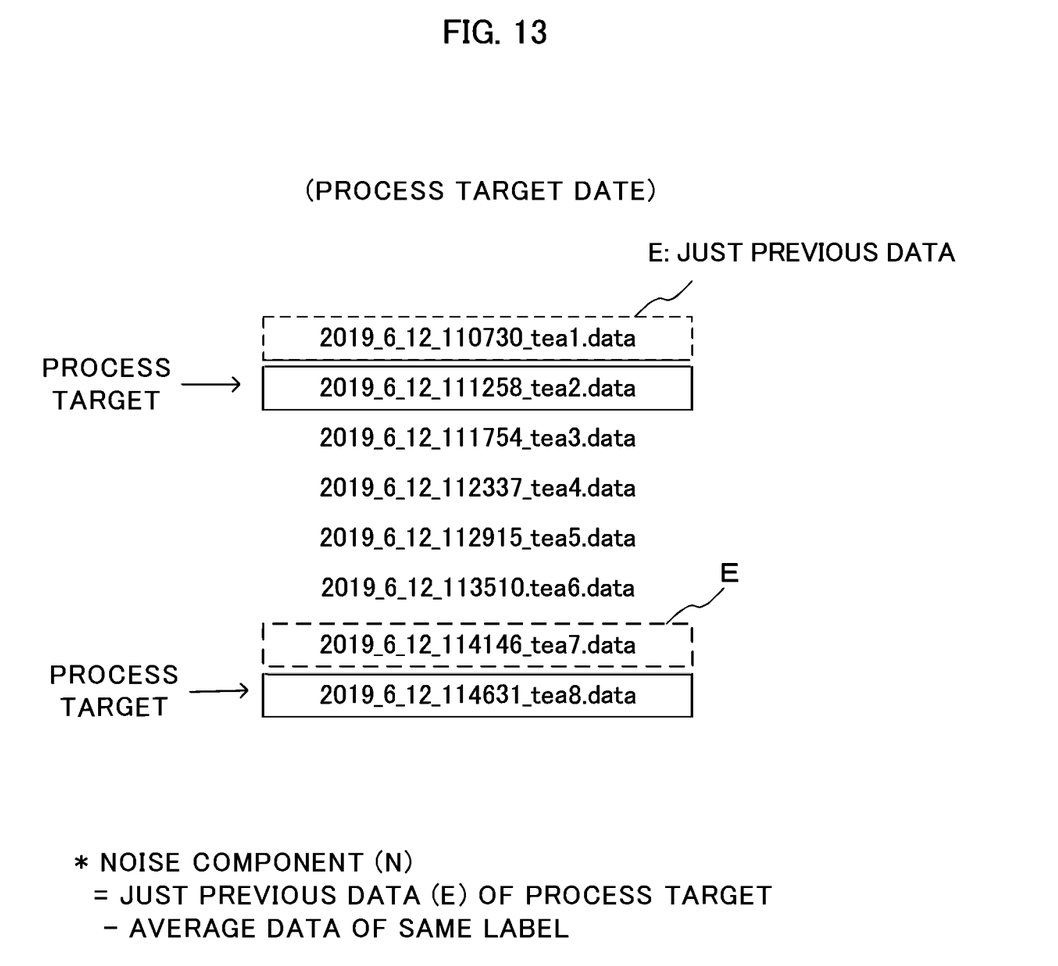
FIG. 13 is a diagram for explaining a noise removing method according to a second example embodiment.

FIG. 13 is a diagram illustrating a noise removal method according to the second example embodiment. As illustrated in FIG. 13, it is assumed that the label "tea1" is first measured by the odor measurement apparatus 10 on the process target date, and then the measurement is performed in an order of "tea2" through "tea8". In this case, when an odor of the label "tea2" is measured, a residual gas concerning the label "tea1" often exists in the odor measurement apparatus 10. Accordingly, using data immediately before data of a process target, a noise component corresponding to the residual gas is extracted.

For example, as illustrated in FIG. 13, in a case where the label "tea2" is the data to be processed, a noise component corresponding to the residual gas of the label "tea1" is extracted by subtracting the average data M of the same label "tea1" from the data E of the label "tea1" immediately before that data. Note that the average data M may be calculated in the same method as in the second example of the first example embodiment described with reference to FIG. 9. In this case, the noise component N is calculated by the following equation.

Noise component ($N$)=data ($E$) immediately before the process target−average data ($M$) for the same label    (3)

Note that the same process may be carried out with respect to other sets of data of the process target date. That is, in an example in FIG. 13, in a case where the data of the label "tea3" are to be processed, the noise component N may be calculated by the equation (3) using the data of the label "tea2" which are data immediately before the data of the label "tea3" and the average data M of the same label "tea2", and may be subtracted from the data of the label "tea3". Similarly, in a case where the data of the label "tea8" is to be processed as illustrated in FIG. 13, the noise component N may be calculated by the equation (3) using the data of the label "tea7" which are the immediately before the data of the label "tea8" and the average data M of the same label "tea7", and may be subtracted from the data of the label "tea8". Although there is no previous data for the first data of the process target date (the label "tea1" in the example in FIG. 13), since it is considered that there is almost no noise component due to the residual gas at the first measurement of the date, it may not be performed the noise removal with respect to the first data of the process target date.

Figure 14:
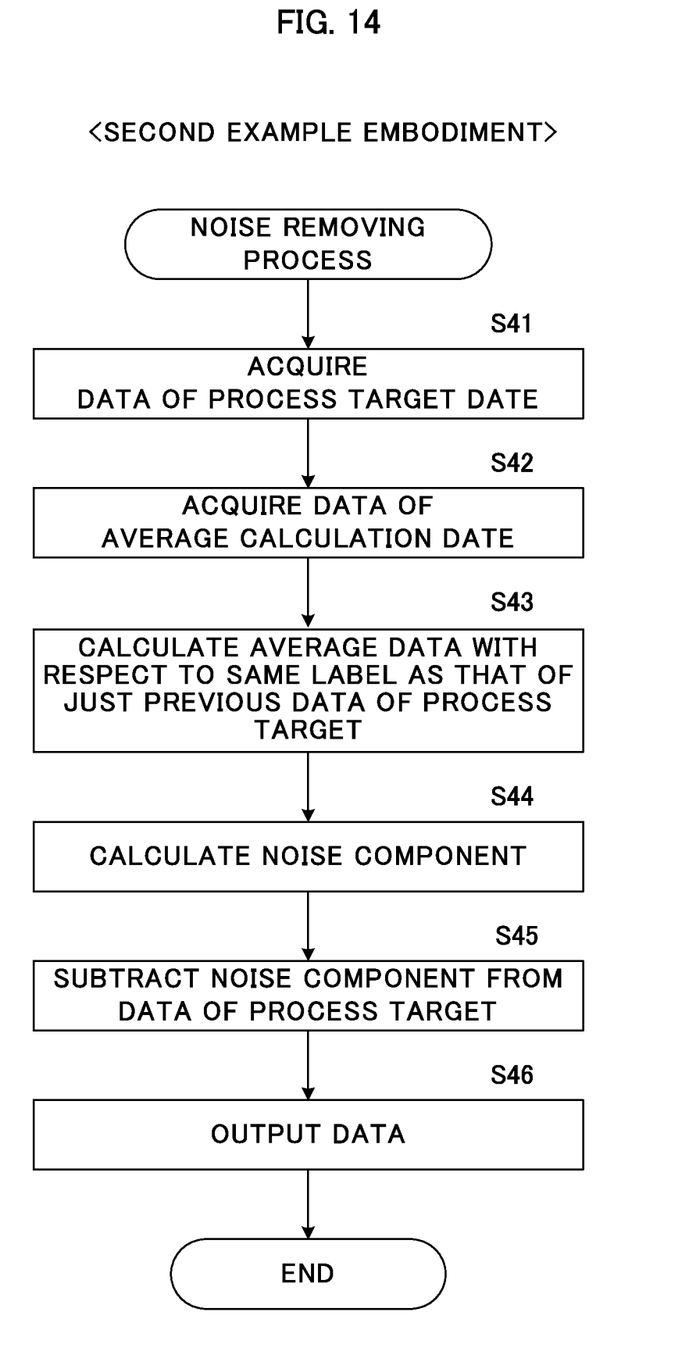
FIG. 14 is a flowchart of a noise removing process according to the second example embodiment.

FIG. 14 is a flowchart of the noise removal process according to the second example embodiment. This process is implemented by the processor 22 illustrated in FIG. 4, which executes a program prepared in advance. First, the data acquisition unit 31 acquires the data of the process target date (step S41), further obtains the data during the average calculation dates (step S42). An order of steps S41 and S42 may be reversed.

Next, the noise component extraction unit 32 determines data as a process target from among the plurality sets of data of the process target date, and calculates the average data M using sets of data during the average calculation dates for the same label as that of data immediately before the data of the process target (step S43). Next, the noise component extraction unit 32 calculates a noise component by subtracting the average data M from data immediately before the process target in accordance with the above equation (3) (step S44), and supplies the calculated noise component to the noise removing unit 33. The noise removing unit 33 subtracts the noise component from the data of the process target (step S45), and outputs the subtracted data as odor data after noise removal (step S26). This noise removal process is performed sequentially for all sets of data of the process target date while changing the data to be processed. After that, the noise removal process is terminated.

(Modification)

In the above example embodiment, the odors of the different labels are measured in order, but a step of measuring an odor of a specific sample may be sandwiched between them. For instance, the measurement of the label "water" is inserted before the measurement of a next label. In this case, the measurement is carried out daily for the label "water", and the average data M are calculated based on sets of the measured data during the average calculation dates. After that, the noise component may be calculated by subtracting the average data M of the "water" prepared in advance from respective sets of the measured data of the "water" immediately before the label to be a process subject.

Furthermore, in the second example embodiment and the modification thereof described above, the noise component N is calculated using the average data M during the average calculation dates, other statistical values other than the average, for instance, a median value for the same label in the average calculation dates or the like may be used.

A part or all of the example embodiments described above may also be described as the following supplementary notes, but not limited thereto.

(Supplementary note 1)

1. A noise removing apparatus comprising:
a data acquisition unit configured to acquire sets of odor data measured using a sensor with respect to a plurality of objects, each set of odor data representing features of an odor of an object by respective rates of a plurality of odor molecules;
a noise component extraction unit configured to extract a noise component using a set of odor data; and
a noise removing unit configured to remove the noise component from each set of odor data to be processed.

(Supplementary note 2)

2. The noise removing apparatus according to supplementary note 1, wherein
the noise component extraction unit subtracts odor data measured on a reference date determined in advance with respect to an object from respective sets of odor data measured for the object on a process target date, and thus extracts a noise component, and
the noise removing unit removes the noise component from the respective sets of odor data of the process target date.

(Supplementary note 3)

3. The noise removing apparatus according to supplementary note 1, wherein
the noise component extraction unit subtracts, from first odor data measured on the process target date, data of a statistical value for a plurality sets of odor data measured with respect to an object of the first odor data before the process target date, and thus extracts a noise component, and
the noise removing unit removes the noise component from respective sets of odor data for each object on the process target date.

(Supplementary note 4)

4. The noise removing apparatus according to supplementary note 3, wherein the statistical value is one of an average value and a median value.

(Supplementary note 5)

5. The noise removing apparatus according to supplementary note 1, wherein
the noise component extraction unit acquires the odor data on the process target date for a specific object determined in advance as a noise component including noise on the process target date; and
the noise removing unit removes the noise component from sets of odor data of each object other than the specific object of the process target date.

(Supplementary note 6)

6. The noise removing apparatus according to supplementary note 1, wherein
the noise component extraction unit subtracts, from odor data measured immediately before odor data of a process target on the process target date, data of a statistical value of a plurality of odor data measured for the same object before the process target date, and thus extracts a noise component; and
the noise removing unit removes the noise component from the odor data of the process target.

(Supplementary note 7)

7. The noise removing apparatus according to supplementary note 6, wherein the statistical value is one of an average value and a median value.

(Supplementary note 8)

8. An odor measurement system comprising an odor measurement apparatus that measures the odor data, and the noise removing apparatus according to supplementary note 6 or 7, wherein
the odor measurement apparatus measures odor data of a specific sample determined in advance between measurements of respective objects, and
the noise component extraction unit subtracts, from the odor data of the specific sample measured immediately before the odor data of the process target on the process target date, data of a statistical value prepared in advance for the specific sample, and thus extracts the noise component.

(Supplementary note 9)

9. A noise removing method, comprising:
acquiring sets of odor data measured using a sensor with respect to a plurality of objects, each set of odor data representing features of an odor of an object by respective rates of a plurality of odor molecules;
extracting a noise component using a set of odor data; and
removing the noise component from each set of odor data to be processed.

(Supplementary note 10)

10. A recording medium storing a program, the program causing a computer to perform a process comprising:
acquiring sets of odor data measured using a sensor with respect to a plurality of objects, each set of odor data representing features of an odor of an object by respective rates of a plurality of odor molecules;
extracting a noise component using a set of odor data; and
removing the noise component from each set of odor data to be processed.

While the disclosure has been described with reference to the example embodiments and examples, the disclosure is not limited to the above example embodiments and examples. It will be understood by those of ordinary skill in the art that various changes in form and details may be made therein without departing from the spirit and scope of the present disclosure as defined by the claims.

DESCRIPTION OF SYMBOLS

5, 6 Database (DB)
10 Odor measurement apparatus

12 Sensor
20 Noise removing apparatus
31 Data acquisition unit
32 Noise component extraction unit
33 Noise removing unit

The invention claimed is:

1. A noise removing apparatus comprising:
a sensor having a deflection membrane, the sensor configured to measure deflection of odor molecules attached to the deflection membrane and output, as odor data, a voltage indicating the measured deflection, where a rate of adhesion and desorption of the odor molecules with respect to the detection membrane is affected by environmental conditions in which the sensor is operating;
a memory storing instructions; and
one or more processors configured to execute the instructions to:
acquire a plurality of sets of the odor data output by the sensor, each set of odor data having a different type;
extract a noise component for each set of the odor data by subtracting the set of the odor data from a reference odor data set corresponding to the different type of the set of the odor data;
remove, from each set of the odor data, the noise component that has been extracted for the set of the odor data; and
output each set of the odor data after removal of the noise component therefrom.

2. The noise removing apparatus according to claim 1, wherein the reference odor data set for each set of the odor data is measured on a reference date determined in advance, and the plurality of sets of the odor data are measured on a process target date.

3. The noise removing apparatus according to claim 1, wherein
the plurality of sets of the odor data are measured on a process target data, and the reference odor data set for each set of the odor data is data of a statistical value for a plurality of other sets of the odor data measured before the process target date.

4. The noise removing apparatus according to claim 3, wherein the statistical value is one of an average value and a median value.

5. The noise removing apparatus according to claim 1, wherein
the plurality of sets of the odor data are for an object, and the reference odor data set for each set of the odor data is for a different object.

6. The noise removing apparatus according to claim 1, wherein
the plurality of sets of the odor data are measured immediately after odor data of a process target is measured on a process target date, and the reference odor data set for each set of the odor data is data of a statistical value for a plurality of other sets of the odor data of the process target measured before the process target date.

7. The noise removing apparatus according to claim 6, wherein the statistical value is one of an average value and a median value.

8. An odor measurement system comprising an odor measurement apparatus that measures the odor data, and the noise removing apparatus according to claim 6, wherein
the odor measurement apparatus measures odor data of a specific sample determined in advance between measurements of respective objects, and
the noise removing apparatus subtracts, from the odor data of the specific sample, data of a statistical value prepared in advance for the specific sample.

9. A noise removing method comprising:
measuring, by a sensor having a deflection membrane, deflection of odor molecules attached to the deflection membrane and output, as odor data, a voltage indicating the measured deflection, where a rate of adhesion and desorption of the odor molecules with respect to the detection membrane is affected by environmental conditions in which the sensor is operating;
acquiring, by a processor, a plurality of sets of the odor data output by the sensor, each set of odor data having a different type;
extracting, by the processor, a noise component for each set of the odor data by subtracting the set of the odor data from a reference odor data set corresponding to the different type of the set of the odor data;
removing, by the processor and from each set of the odor data, the noise component that has been extracted for the set of the odor data; and
outputting, by the processor, each set of the odor data after removal of the noise component therefrom.

10. A non-transitory recording medium storing a program executable by a computer to perform a process comprising:
receiving output from a sensor having a deflection membrane, the sensor configured to measure deflection of odor molecules attached to the deflection membrane and output, as odor data, a voltage indicating the measured deflection, where a rate of adhesion and desorption of the odor molecules with respect to the detection membrane is affected by environmental conditions in which the sensor is operating;
acquiring a plurality of sets of the odor data output by the sensor, each set of odor data having a different type;
extracting a noise component for each set of the odor data by subtracting the set of the odor data from a reference odor data set corresponding to the different type of the set of the odor data;
removing, from each set of the odor data, the noise component that has been extracted for the set of the odor data; and
outputting each set of the odor data after removal of the noise component therefrom.

* * * * *